(12) United States Patent
Castillo

(10) Patent No.: US 10,946,054 B1
(45) Date of Patent: Mar. 16, 2021

(54) THERAPEUTIC CANNABIS EXTRACTS

(71) Applicant: Jenny's Rose, LLC, Los Angeles, CA (US)

(72) Inventor: James Castillo, San Diego, CA (US)

(73) Assignee: Jenny's Rose, LLC, Los Angeles, CA (US)

( * ) Notice: Subject to any disclaimer, the term of this patent is extended or adjusted under 35 U.S.C. 154(b) by 0 days.

(21) Appl. No.: 16/596,287

(22) Filed: Oct. 8, 2019

(51) Int. Cl.
| | |
|---|---|
| *A61K 36/00* | (2006.01) |
| *A61K 36/185* | (2006.01) |
| *A61K 31/352* | (2006.01) |
| *A61K 31/685* | (2006.01) |
| *A61K 31/015* | (2006.01) |
| *A61K 31/105* | (2006.01) |

(52) U.S. Cl.
CPC .......... *A61K 36/185* (2013.01); *A61K 31/015* (2013.01); *A61K 31/105* (2013.01); *A61K 31/352* (2013.01); *A61K 31/685* (2013.01)

(58) Field of Classification Search
CPC ...................................................... A61K 36/00
USPC ......................................................... 424/725
See application file for complete search history.

(56) References Cited

U.S. PATENT DOCUMENTS

| | | |
|---|---|---|
| 10,195,159 B2 | 2/2019 | Whittle et al. |
| 2016/0324776 A1* | 11/2016 | Glatzel ................... A23F 3/163 |

FOREIGN PATENT DOCUMENTS

| | | |
|---|---|---|
| WO | 2018187500 A1 | 11/2018 |

* cited by examiner

*Primary Examiner* — Michael V Meller
(74) *Attorney, Agent, or Firm* — Stefan J. Kirchanski; Matthew J. Spark; Zuber Lawler LLP

(57) ABSTRACT

The present invention may be one of several formulations containing cannabinoids and non-cannabinoid compounds. Cannabis plants are subjected to extraction, and the resulting extract may be supplemented with additional ingredients to achieve a desired chemical profile. Dose titration may be used to find an appropriate dose of cannabis extract to be ingested in treating medical conditions.

32 Claims, No Drawings

THERAPEUTIC CANNABIS EXTRACTS

BACKGROUND OF THE INVENTION

The cannabis plant (*Cannabis sativa* L.) ("cannabis") naturally produces a complex mixture of compounds (often called "natural products" or "secondary metabolites"), including cannabinoids, flavonoids and terpenoids which are present in much higher concentrations in the female inflorescences than in other parts of the plant. The precise function of these compounds within the plant is largely unknown; it is generally hypothesized that many of the compounds are used defensively to prevent predation by animals and attack by fungi and bacteria. After cannabis is harvested, these compounds can be isolated by means of an extraction process. Cannabinoids are natural products that are largely exclusive to the cannabis plant. While over one hundred cannabinoids are known, only the most prevalent ones are generally analyzed when characterizing cannabis for medicinal or recreational purposes.

Some cannabinoids ("primary cannabinoids") are present in the common cultivars (AKA "strains") of cannabis known to date and include cannabidiolic acid ("CBDA"), cannabigerol acid ("CBGA"), and tetrahydrocannabinolic acid ("THCA"). It will be appreciated that the cannabis plant produces the carboxylic acid form of cannabinoids (e.g., THCA). During the extraction processes, the naturally occurring acidic forms are typically converted into physiologically active decarboxylated forms (e.g., CBD, THC, CBG) for the final extract. Some of the other cannabinoids ("common cannabinoids") are also commonly found in cannabis, but they usually exist at lower overall concentrations, with greater variation in concentration from strain to strain and their availability in the final extract may also be contingent on the extraction process. These include cannabinoid compounds such as: $\Delta$8-tetrahydrocannabinolic acid ("$\Delta$8-THCA"); tetratetrahydrocannabivarin ("THCV"); tetrahydrocannabivarinic acid ("THCVA"); cannabichromene ("CBC"); cannabichromenic acid ("CBCA"). Cannabinol (CBN), typically formed as a breakdown product of THC, is found in aging cannabis plants, as the endogenous cannabinoid is exposed to high temperature and sunlight. CBDA is present at a relatively high level in a few medicinal/recreational cannabis cultivars but is generally associated with "hemp" cannabis cultivars which normally contain appreciable levels of CBDA (and the decarboxylated form CBD). Terpenoids common in cannabis include compounds such as: D-limonene; linalool; eucalyptol (also known as 1,8-cineol); $\alpha$-pinene; terpinen-4-ol (also known as 4-terpineol); p-cymene; borneol; $\Delta$-3-carene; pulegone; $\beta$-myrcene; humulene; and $\beta$-sitosterol (a phytosterol). Flavonoids present in cannabis include cannflavin A; apigenin; and quercetin. The level of the various terpenoids and flavonoids vary greatly from cultivar to cultivar. In summary, medicinal/recreational cultivars of cannabis contain high levels of one or more of the primary cannabinoids. They also contain variable levels of the one or more of the "common cannabinoids." Generally, the primary and common cannabinoids are the ones that are analyzed for in the industry. The other seventy-five or more "minor cannabinoids" are typically not currently analyzed in the industry, but it is believed that most cultivars contain at least some of the minor cannabinoids.

Although terpenoids and flavonoids are known to have potential medical benefit, medical as well as recreational effects of cannabis have been generally attributed to cannabinoids—particularly the primary cannabinoids. The major psychoactive cannabinoid is THC. While CBD is not considered to have the significant psychoactive properties as does THC, it is now known to interact with THC and modulate the biological effect of THC. The story is even more complicated because it is becoming recognized that major and minor cannabinoids interact with each other as well as with terpenoids and possibly other plant natural products to produce medical and recreational effects that cannot be attributed to cannabinoids alone. This interaction or synergy resulting from the complex mixture of compounds present within cannabis is variously known as the "entourage effect," in which a mixture of compounds demonstrates greater efficacy in treating a medical condition than any of its constituent compounds in isolation.

The existence of the entourage effect calls into question the conventional wisdom underlying commercial cannabis-derived pharmaceuticals, which dictates that particular compounds should be isolated from cannabis and refined to high purity. For example, the drug Epidiolex® (marketed by GW Pharmaceuticals, plc) identifies only CBD as the active pharmaceutical ingredient on its label. The drug Sativex® (marketed by GW Pharmaceuticals, plc), which is currently undergoing clinical trials, indicates that a mixture of CBD and $\Delta$9-THC, both from plant derived sources, are the active pharmaceutical ingredients.

Extraction processes, especially those directed at pharmaceutical compositions, have focused on preparing plant extracts that are rich in individual cannabinoids at the expense of other plant natural products. Typical extraction processes involve a "winterization" step where waxes and lipids that are extracted when the plant cells and organelles are ruptured during the extraction process and are removed from the extract by subjecting the extract to subzero temperatures which solidifies or freezes the waxes and lipids. Such waxes and lipids are viewed in the industry as undesirable impurities that affect the stability, potency, and overall desirability of the cannabis extract.

U.S. patent Ser. No. 10/195,159 (the '159 Patent) describes a process for removing what it describes as the unwanted "ballast" from cannabis plant extracts. The ballast described therein includes plant cell constituents comprising "fats, waxes, carbohydrates, proteins and sugars." The inventors explain that "[t]he presence of these substances results in botanical extracts which may be hygroscopic, difficult to reduce to a powder and generally intractable as starting materials for pharmaceutical preparations." The '159 Patent explains "that presence of ballast may also limit the shelf-life of pharmaceutical products formulated from such extracts." The '159 Patent also explains that some elements of ballast can be "removed by an additional step post-extraction referred to as "winterization", which involves making a concentrated solution of the extract and cooling it to a temperature at which a proportion of waxes and lipid components may be precipitated, typically −20° C."

WO2018187500A1 (the '500 Application) describes a process for removing waxes and lipids from crude cannabis extracts before the process of decarboxylation and purification of the extracts to obtain purified cannabis extracts. The '500 Application explains that crude cannabis extracts are known to contain high concentration of waxes and hydrocarbons from plant materials. Such waxes and plant materials are typically removed or reduced by a "winterization process" prior to decarboxylation and purification of the cannabis extract. The "winterization process" is typically performed by dissolving the distillate in alcohol which is then subjected to subzero temperatures to separate out the fats and waxes. In the '500 Application, the winterization process involves dissolving the distillate in 200-proof ethanol and then placing in the resulting solution in a freezer at −20° C. for 4 hours. While cold, the precipitated material containing the unwanted fats and waxes was filtered using a filter funnel, and the filter was rinsed with 100 ml of ice cold ethanol. The filtered ethanolic solution of the distillate was evaporated to dryness to give 84.0 g residue (78% CBD content). The '500 Application described that the CBD recovery in this step is 99.0%, demonstrating that the typical extraction process focuses on removing waxes and lipids during the extraction process, in favor of producing a concentrated cannabinoid.

Surprisingly, it has been found that the fraction that is typically discarded, containing the waxes and lipids, is important to the therapeutic value of the extract. This is because it is becoming recognized that the plant's therapeutic value may not be attributable to the major cannabinoids alone. Rather, the therapeutic value may lie in a synergistic effect between numerous chemical components present in the cannabis plants. This interaction or synergy resulting from the complex mixture of compounds present within the cannabis plant is variously known as the "entourage effect," in which a mixture of compounds present demonstrates greater therapeutic efficacy than any of its constituent compounds in isolation. Accordingly, there is a need for therapeutic cannabis products which recognize the importance of having multiple cannabinoids, terpenoids, and other active molecules including waxes and lipids that facilitate entourage effects.

SUMMARY OF THE INVENTION

The present invention encompasses novel cannabinoid formulations—primarily for oral administration—that contain target concentrations of cannabinoids, and other cannabis-plant derived fractions which show synergistic activities not found in combinations of purified cannabinoids. The formulations may be prepared by combining the individual cannabinoids, terpenoids, and the "remainder fraction," to achieve the target composition. The cannabinoids and terpenoids can be derived from various types of extracts of cannabis and other plants.

The formulations may also be prepared by selecting cannabis cultivars known to have cannabinoid profiles close to the target combinations and supplementing the extracts as needed to reach the target formulations. The cannabis extracts may be produced by subjecting harvested cannabis from known cultivars such as afghani, skunk, white widow, blue dream, and AC/DC (also known as ACDC) strains to an extraction process. It will be appreciated that using certain known cultivars as starting materials may facilitate producing extracts with certain preferred levels of active ingredients. These named cultivars are merely examples, and the cultivar of choice will depend on the target concentrations of active compounds desired in the final formulation. The extraction process may use an alcohol, such as ethanol, or a non-polar compound, such as butane, as the extraction solvent. The cannabis extract may also be supplemented by adding active compounds from independent sources. Alternatively, purified extracts of individual cannabinoids, terpenoids and other active plant compounds may be combined to create the formulations to obtain improved therapeutic outcomes.

A goal of the inventive formulations is to take advantage of the entourage effect. In the typical extraction process, the goal is to obtain purified extracts containing high concentrations of the cannabinoids, and discarding portions of the extract containing waxes, lipids, and other components of plant materials that do not contain the desired cannabinoids. As such portions of the extracts do not contain cannabinoids, they are not believed to possess therapeutic or commercial value.

For example, cold liquid butane or cold ethanol may be used to extract ground cannabis material. The plant material is retained by an about 220 μm screen or similar filter, and the extraction solvent is allowed to flow through. Prior to removal of the extraction solvent, the extract mixture is filtered to remove small particles of plant material. The inventor has found that filtration using filters having about a 45 μm pore size removes the vast majority of plant solids (i.e., insoluble bits of plant tissue). Next, the extract is optionally filtered through a filter having a 5 μm pore size which passes the dissolved extract compounds and retains a "remainder" fraction. Details of this process are found in copending U.S. patent application Ser. No. 16/569,535, titled "NOVEL ACTIVE FRACTION FROM THERAPEUTIC CANNABIS PLANT EXTRACTS, filed 12 Sep. 2019, the contents of which are incorporated herein by reference. The majority of the solvent extract which passes through the filter(s) is used to produce a "mixed cannabinoid" fraction. The "remainder" fraction recovered from the 5 μm filter consists of particles or micelles of waxes and/or other lipids and would normally be discarded. The inventor has made the surprising discovery that adding a significant percentage of the "remainder" to the final formulation greatly enhances the effectiveness of the formulation—showing a magnified "entourage-like" effect. The reason for this effect is under current investigation. It is possible that the presence of certain waxes and/or other lipids may improve the absorption of the formulation by the individual, thereby enhancing the physiological actions of the cannabinoid formulation.

The cannabis formulations described herein can be administered to a patient to alleviate a variety of maladies including Parkinson's disease, pain symptoms, inadequate appetite, inflammation, and sleep disorders. For any given patient, the optimal dosage of the formulation may be determined by performing a dose titration over an extended period.

DETAILED DESCRIPTION OF THE INVENTION

Definitions: The following terms may be used as a shorthand to discuss cannabinoids. They are for convenience only. "Primary cannabinoids" are found in many or most cannabis cultivars currently available. These are CBDA, CBGA, and THCA, or their decarboxylated equivalents. Most cultivars have high levels (greater than about 5% by weight of dried plant material) of one or more of the primary cannabinoids or their decarboxylated equivalents. "Common cannabinoids" are present at lower levels in most cultivars and include Δ8-THC, THCVA, CBCA and their decarboxylated equivalents; any cannabinoid that is routinely analyzed for and is not a primary cannabinoid is considered a common cannabinoid. "Minor cannabinoids" are those cannabinoids not routinely analyzed for. It will be appreciated that the list of "routinely" analyzed cannabinoids is influenced by several factors. Regulations may dictate that Δ9-THC content and the content of some other primary cannabinoids be listed on the product. Experimental or anecdotal evidence may suggest the efficacy of certain minor cannabinoids—this creates the impetus to analyze for those cannabinoids. As a result, the newly analyzed cannabinoids move from the "minor cannabinoid" grouping to the "common cannabinoid" grouping. "Mixed cannabinoids fraction" is the fraction produced when a crude cannabis extract is refined to remove solvents and other undesirable components.

"Remainder" fraction is the fraction removed from crude cannabis extracts by filtration or an equivalent separation technique (e.g., centrifugation). After the extraction process the crude extract (solvent and dissolved plant compounds) is cloudy indicating that it still contains undissolved material. Filtration of the crude cannabis extract through a filter having about a 45 µm pore size removes most of the undissolved plant material yielding a somewhat cloudy filtrate. Filtration of the 45 µm filtrate through a filter having about a 5 µm pore size yields a clear filtrate containing the dissolved cannabinoids and other dissolved cannabis compounds. The material remaining on the 5 µm filter is the remainder fraction. This remainder fraction contains active compounds, probably in the form of micelles or compounds absorbed to very small particles of plant material that significantly enhance the effectiveness of a given formulation through an entourage-like effect. The remainder fraction may be scraped off the filter and used immediately. If the remainder fraction is to be stored for an appreciable period of time, it should be washed off the filter with solvent and stored at low temperatures. For use, the remainder fraction is recovered from the suspension by filtration or centrifugation.

For example, quantity of harvested cannabis is first converted to cannabis extract. Production of the cannabis extract may be performed using the method set forth in co-pending U.S. patent application Ser. No. 16/365,614, entitled "Producing Cannabis Extracts via Selective Decarboxylation" which was filed on Mar. 26, 2019, the contents of which are incorporated herein by reference. Alternatively, extraction may be performed using butane as a solvent or any other extraction method practiced in the art of producing plant extracts.

Unless otherwise stated, the concentration of any compound in a cannabis extract (oil) or cannabis formulation is stated as a percentage based on weight. Thus, a Δ9-THC concentration of 24% by weight means that 24 mg of Δ9-THC are present in every 100 mg. Likewise, a formulation having a CBD concentration of 48% by weight means 48 mg of CBD are present in every 100 mg of the formulation. The therapeutic formulation may be supplemented by the addition of active compounds from separate sources (e.g., black pepper extract). Unless otherwise stated, the amounts of separately added liquid ingredients in a cannabis extract or formulation are expressed as a percentage based on volume. Thus, a formulation that contains 1% black pepper extract by volume contains 1 ml of black pepper extract in every 100 ml of the formulation.

According to the present invention a cannabis formulation typically is supplemented with remainder fraction at a concentration of 10%-40% by weight (i.e., the added remainder accounts for 10-40 mg of weight in every 100 mg of the formulation). The presence of remainder compounds in a cannabis formulation allows the formulation to exhibit an enhanced entourage effect in therapeutic use. To further enhance the entourage effect, a cannabis formulation may be supplemented with terpene/terpenoids-containing extracts. Such extracts can be obtained from RICCA Chemical Company, LLC of Arlington, Tex. Unless otherwise indicated, extracts containing linalool, α-pinene, β-myrcene, and D-limonene were supplied by RICCA. A cannabis formulation may also be supplemented with black pepper extract and Ceylon cinnamon bark oil supplied, for example, by Botanicals by the Sea LLC of Carlsbad, Calif.; and cinnamon cassia oil supplied by Botanicals by the Sea LLC of Carlsbad, Calif. Equivalent extracts are readily available from other suppliers and are equally suitable.

The following formulations are those tested and perfected by the inventor. They are but exemplars of the general principles presented here. Although based on cannabis extract (or cannabis "oil" as it is often known in the trade) the final volume of a formulation is reached by adding cannabinoid-free hemp oil as a diluent/carrier. The various active compounds are soluble in the carrier which decreases the viscosity of the formulation while significantly increasing the absorption and bioavailability of the formulation. Lecithin, such as natural sunflower lecithin, may be added as an emulsifier.

Each formulation is built around the ratios of different cannabinoids. For example, the ratio of CBD to THC. The addition of terpenoids further promotes the entourage effect established by the cannabinoids. It is possible to establish the desired ratio of the cannabinoids by combining purified cannabinoids (e.g., from cannabis extracts or distillates). The ratios may also be achieved by using mixed cannabinoid fractions from defined cultivars. Active terpenoids may come from the cannabis extracts. Additional active terpenoids from other botanical sources are added to make the final formulation. Finally "remainder" fraction, preferably from defined cultivars, is added to complete the formulation. In general, after the required amounts of the cannabinoids have been added, a sufficient weight of remainder fraction is added to bring the total weight of the cannabinoid component to 100%. (It should be understood that while the remainder fraction may not contain cannabinoids, it is treated like a cannabinoid from weight percent basis for formulation purposes.)

Formulation Examples

1) Δ8-THC Enriched Formulation ("Formulation C"). In this embodiment, cannabis component contains about: 0.3% or less Δ9-THC by weight; 20% CBD by weight; 1% CBDA by weight; 3% CBN by weight; and 60% Δ8-THC by weight (approximately 84% total cannabinoids by weight) plus about 16% by weight remainder fraction to make approximately 100%. The final formulation may compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; be 0.05-3% cassia cinnamon oil (*Cinnamomum aromaticum*) by volume; and 0.05-3% Ceylon cinnamon bark oil (*Cinnamomum verum*) by volume.

2) High CBD Non-psychoactive, Non-decarboxylated Formulation. In this embodiment, the cannabinoid component is preferably derived from an extract of white widow or AC/DC cultivars. The cannabis component contains about: 2% Δ9-THC by weight; 24% THCA by weight; 1% CBD by weight; 48% CBDA by weight; 3% CBN by weight; 4% Δ8-THC by weight; 3% CBG by weight; and 1%-3% THCV by weight. These cannabinoids can be derived from other sources. Remainder fraction is added to bring the cannabinoid total weight to about 100%. The final formulation is compounded by supplementing this base, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

3) CBD Decarboxylated Formulation. A quantity of cannabis extract produced from the white widow or AC/DC cultivars is first subjected to decarboxylation through heat treatment as is well-known in the art. After decarboxylation, the cannabis extract contains about: 24% Δ9-THC by weight; 2% THCA by weight; 48% CBD by weight; 1% CBDA by weight; 3% CBN by weight; 4% Δ8-THC by weight; 3% CBG by weight; and 1-3% THCV by weight. (The basic THC:CBD ratio is about 1:2.) Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

4) AC/DC Non-Decarboxylated Formulation. In this embodiment, harvested cannabis from the AC/DC strain is subjected to an extraction process. The resulting cannabis extract contains about: 3% Δ9-THC by weight; 10% THCA by weight; 60% CBD by weight; 1% CBDA by weight; 3% CBN by weight; 1% Δ8-THC by weight; 4% CBG by weight; and 1%-3% THCV by weight. Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

5) Hemp-based Formulation. In this embodiment, harvested cannabis meeting the definition of "hemp" set forth in the Agriculture Improvement Act of 2018 is subjected to an extraction process. The resulting cannabis extract contains Δ9-THC and THCA that are within the legal limit for hemp (i.e., less than 0.3% on a dry weight basis). The cannabis extract additionally contains about: 65%-75% CBD by weight; 1% CBDA by weight; 5%-15% CBN by weight. The cannabis extract contains essentially no Δ8-THC, CBG, or THCV. Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

6) Blue Dream plus AC/DC Formulation ("Formulation A"). In this embodiment, harvested cannabis from the blue dream and AC/DC strains (approximately equal quantities of each strain) are subjected to an extraction process. The resulting cannabis extract contains about: 35% Δ9-THC by weight; 35% CBD by weight; 3% CBN by weight; 3% Δ8-THC by weight; and 4% CBG by weight. The THC:CBD ratio is about 1:1. The cannabis extract contains essentially no CBDA or THCV. Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

7) Afghani plus Skunk plus AC/DC Formulation ("Formulation B"). In this embodiment, harvested cannabis from the afghani, skunk, and AC/DC cultivars (approximately equal quantities of each strain) is subjected to an extraction process. The resulting cannabis extract contains about: 35% Δ9-THC by weight; 35% CBD by weight; 3% CBN by weight; 3% Δ8-THC by weight; and 4% THCV by weight. The THC:CBD ratio is about 1:1. The cannabis extract contains essentially no CBG. Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

8) Critical Mass Formulation. In this embodiment, harvested cannabis from the critical mass strain is subjected to an extraction process. The resulting cannabis extract contains about: 3% CBN by weight; 3% Δ8-THC by weight; and 4% CBG by weight. The final formulation should contain Δ9-THC and CBD at a 1-to-1 ratio, or 45% by weight each. Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

9) Catatonic Formulation. In this embodiment, harvested cannabis from the catatonic strain is subjected to an extraction process. The resulting cannabis extract contains about: 3% CBN by weight; 3% Δ8-THC by weight; and 4% CBG by weight. The final cannabis formulation should contain Δ9-THC and CBD at a 2-to-1 ratio, or 60% by weight of THC and 20% by weight of CBD. Remainder fraction is added to bring the cannabinoid total weight to about 100%. The final formulation is compounded by supplementing this base extract, using cannabis-derived or compounds derived from other botanicals, to contain: 0.05%-1% linalool by weight; 0.05%-1% α-pinene by weight; and 0.05%-1% β-myrcene by weight. The resulting cannabis formulation may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

10) Sleep Aid Formulation. This embodiment is intended as a sleep aid. The dominant cannabinoid is CBN (about 60%). It also contains a relatively high percentage of CBD—about 20% plus about 1% CBDA. In addition, it contains about 3% THC and about 1% THCA. The formula also contains about 4% CBG and about 1% Δ8-THC with about 10% remainder. The desired terpenoid content is between about 1% and 4% by weight terpenoids. The percentage breakdown of the terpenoids is about 2% limonene, about 9% linalool, about 6.5% α-pinene, about 5% α-terpineol, about 5% valencene, about 4.5% α-bisabolol, about 43% β-myrcene, about 13% β-caryophyllene, about 5% β-ocimene and about 8% α-humulene. In addition, the formulation contains 5% lecithin by volume and may additionally be supplemented to contain: 0.05%-3% black pepper extract (source of β caryophyllene) by volume; 0.05-3% cassia cinnamon oil (*Cinnamomum aromaticum*) by volume; and 0.05-3% Ceylon cinnamon bark oil (*Cinnamomum verum*) by volume.

The following claims are thus to be understood to include what is specifically illustrated and described above, what is conceptually equivalent, what can be obviously substituted and what incorporates the essential idea of the invention. Those skilled in the art will appreciate that various adaptations and modifications of the just-described preferred embodiments can be configured without departing from the scope of the invention. The illustrated embodiment has been set forth only for the purposes of example and that should not be taken as limiting the invention.

What is claimed is:

1. An emulsion consisting essentially of a cannabis extract, a Ceylon cinnamon bark oil, a black pepper extract, and lecithin.

2. The emulsion of claim 1, wherein the cannabis extract is about 20% Cannabidiol by weight, about 60% Δ8-Tetrahydrocannabinol by weight and less than about 5% by weight of other cannabinoids.

3. The emulsion of claim 1, further consisting essentially of 1-4% by weight added terpenoid compounds.

4. The emulsion of claim 3, wherein the added terpenoid compounds consist essentially of about 0.05%-1% linalool by weight, about 0.05%-1% α-pinene by weight and about 0.05%-1% β-myrcene by weight.

5. The emulsion of claim 1, wherein the cannabis extract is about 24% Tetrahydrocannabinolic acid by weight and about 48% Cannabidiolic Acid by weight.

6. The emulsion of claim 5, wherein the cannabis extract is about 2% Tetrahydrocannabinol by weight, about 1 Cannabidiol by weight, about 3% Cannabinol by weight, about 4% Δ8-Tetrahydrocannabinol by weight, about 3% Cannabigerol by weight and about 1-3% Tetrahydrocannabivarin by weight.

7. The emulsion of claim 6, further consisting essentially of about 1-4% by weight added terpenoid compounds.

8. The emulsion of claim 7, wherein the added terpenoid compounds consist essentially of about 0.05%-1% linalool by weight, about 0.05%-1% α-pinene by weight and about 0.05%-1% β-myrcene by weight.

9. The emulsion of claim 1, wherein the cannabis extract is about 24% Tetrahydrocannabinol by weight and about 48% Cannabidiol by weight.

10. The emulsion of claim 9, wherein the cannabis extract is about 2% Tetrahydrocannabinolic acid by weight, about 1% Cannabidiolic Acid by weight, about 3% Cannabinol by weight, about 3% Cannabigerol by weight and about 1-3% Tetrahydrocannabivarin by weight.

11. The emulsion of claim 9, further consisting essentially of about 1-4% by weight added terpenoid compounds.

12. The emulsion of claim 11, wherein the added terpenoid compounds consist essentially of about 0.05%-1% linalool by weight, about 0.05%-1% α-pinene by weight and about 0.05%-1% β-myrcene by weight.

13. The emulsion of claim 9, wherein the black pepper extract is about 0.05%-3% black pepper extract by volume.

14. The emulsion of claim 9, further consisting essentially of about 0.05-3% cassia cinnamon oil by volume.

15. The emulsion of claim 10, wherein the Ceylon cinnamon bark oil is about 0.05-3% by volume.

16. The emulsion of claim 1, wherein the cannabis extract is about 10% Tetrahydrocannabinolic acid and about 60% Cannabidiol.

17. The emulsion of claim 16, wherein the cannabis extract is about 3% Tetrahydrocannabinol by weight, about 1 Cannabidiolic Acid by weight, about 3% Cannabinol by weight, about 1% Δ8-Tetrahydrocannabinol by weight, about 4% Cannabigerol by weight and about 1-3% Tetrahydrocannabivarin by weight.

18. The emulsion of claim 17, further consisting essentially of about 1-4% by weight added terpenoid compounds of 1-4% by weight.

19. The emulsion of claim 18, wherein the added terpenoid compounds consist essentially of about 0.05%-1% linalool by weight, about 0.05%-1% α-pinene by weight and about 0.05%-1% β-myrcene by weight.

20. The therapeutic formulation of claim 19, wherein the added terpenoid compounds consist essentially of about 0.05%-1% linalool by weight, about 0.05%-1% α-pinene by weight and about 0.05%-1% β-myrcene by weight.

21. The emulsion of claim 20, wherein the added terpenoid compounds consist essentially of about 0.05%-1% linalool by weight, about 0.05%-1% α-pinene by weight and about 0.05%-1% β-myrcene by weight.

22. The emulsion of claim 21, wherein the added terpenoid compounds consist essentially of about 0.05%-1% linalool by weight, about 0.05%-1% α-pinene by weight and about 0.05%-1% β-myrcene by weight.

23. The emulsion of claim 1, wherein the cannabis extract is about equal amounts by weight of Tetrahydrocannabinol and Cannabidiol and less than 5% by weight of Cannabinol, Tetrahydrocannabinol, and Cannabigerol.

24. The emulsion of claim 23, wherein the cannabis extract is at least 30% Tetrahydrocannabinol by weight, and at least 30% Cannabidiol by weight.

25. The emulsion of claim 24, further consisting essentially of about 1-4% by weight added terpenoid compounds.

26. The emulsion of claim 25, wherein the added terpenoid compounds consist essentially of about 0.05%-1% linalool by weight, about 0.05%-1% α-pinene by weight and about 0.05%-1% β-myrcene by weight.

27. The emulsion of claim 1, wherein the cannabis extract is of about 24% Tetrahydrocannabinol by weight and about 48% Cannabidiol by weight.

28. The emulsion of claim 1, wherein the cannabis extract is about 60% Tetrahydrocannabinol by weight, about 20% Cannabidiol by weight, about 3% Cannabinol by weight, about 3% Δ8-Tetrahydrocannabinol by weight, and about 4% Cannabigerol by weight.

29. The emulsion of claim 28, further consisting essentially of about 1-4% by weight added terpenoid compounds.

30. The emulsion of claim 29, wherein the added terpenoid compounds consist essentially of about 0.05%-1% linalool by weight, about 0.05%-1% α-pinene by weight and about 0.05%-1% β-myrcene by weight.

31. The emulsion of claim 1, wherein the cannabis extract is about 20% Cannabidiol by weight and about 60% Cannabinol by weight.

32. The emulsion of claim 31, wherein the cannabis extract is about 3% Tetrahydrocannabinol by weight, about 1 Tetrahydrocannabinolic acid by weight, about 1% Δ8-Tetrahydrocannabinol by weight, and about 4% Cannabigerol by weight; added terpenoid compounds of 1%-4% by weight wherein the added terpenoid compounds consist essentially of about 2% limonene, about 9% linalool, about 6.5% α-pinene, about 2% α-terpineol, about 5% valencene, about 4.5% α-bisabolol, about 43% β-myrcene, about 13% β-caryophyllene, about 5% β-ocimene and about 8% α-humulene by weight; and about 5% lecithin by volume.

* * * * *